United States Patent
Abiko et al.

(10) Patent No.: US 9,637,638 B2
(45) Date of Patent: May 2, 2017

(54) IRON OXIDE-COATED LAYERED SILICATE PIGMENT

(71) Applicant: TOPY KOGYO KABUSHIKI KAISHA, Tokyo (JP)

(72) Inventors: Masahiro Abiko, Toyohashi (JP); Ryuichi Seike, Toyohashi (JP); Tomohiro Hoshino, Toyohashi (JP)

(73) Assignee: TOPY KOGYO KABUSHIKI KAISHA, Tokyo (JP)

( * ) Notice: Subject to any disclaimer, the term of this patent is extended or adjusted under 35 U.S.C. 154(b) by 135 days.

(21) Appl. No.: 14/373,422

(22) PCT Filed: Jan. 23, 2013

(86) PCT No.: PCT/JP2013/051279
§ 371 (c)(1),
(2) Date: Jul. 21, 2014

(87) PCT Pub. No.: WO2013/111771
PCT Pub. Date: Aug. 1, 2013

(65) Prior Publication Data
US 2015/0005393 A1  Jan. 1, 2015

(30) Foreign Application Priority Data

Jan. 23, 2012 (JP) ................................ 2012-011283

(51) Int. Cl.
*C09C 1/28* (2006.01)
*A61Q 1/10* (2006.01)
(Continued)

(52) U.S. Cl.
CPC .................. *C09C 1/28* (2013.01); *A61K 8/25* (2013.01); *A61Q 1/10* (2013.01); *A61Q 3/02* (2013.01);
(Continued)

(58) Field of Classification Search
CPC ......... A61Q 1/10; A61Q 3/02; C01P 2006/62; C01P 2006/63; C01P 2006/64;
(Continued)

(56) References Cited

U.S. PATENT DOCUMENTS 3,087,828 A   4/1963   Linton
3,087,829 A   4/1963   Linton
(Continued)

FOREIGN PATENT DOCUMENTS

EP   1672036 A1   6/2006
JP   S4325644     11/1968
(Continued)

OTHER PUBLICATIONS

International Search Report dated Apr. 16, 2013 filed in PCT/JP2013/051279.
(Continued)

*Primary Examiner* — Shuangyi Abu Ali
(74) *Attorney, Agent, or Firm* — Rankin, Hill & Clark LLP

(57) ABSTRACT

The present invention provides an iron oxide-coated layered silicate pigment that has no interference color, strongly exhibits the color inherent in iron oxide, and is excellent in gloss. The pigment of the present invention is an iron oxide-coated layered silicate pigment comprising a layered-silicate plate particle as base, and an iron oxide coated on the plate particle; wherein the iron oxide does not coat the surface portion of the plate particle or the iron oxide is localized on the edge portion rather than the surface portion of the plate particle. As the iron oxide, at least one kind selected from black iron oxide ($Fe_3O_4$) and red iron oxide ($Fe_2O_3$) can be used preferably. As the layered silicate, a mica-group layered silicate can be used preferably. The iron
(Continued)

oxide-coated layered silicate pigment of the present invention can be incorporated into cosmetic preferably.

14 Claims, 5 Drawing Sheets

(51) Int. Cl.
    *A61Q 3/02*                  (2006.01)
    *A61K 8/25*                  (2006.01)
    *C09C 1/00*                  (2006.01)

(52) U.S. Cl.
    CPC ........ *C09C 1/0021* (2013.01); *A61K 2800/26* (2013.01); *A61K 2800/621* (2013.01); *C01P 2006/62* (2013.01); *C01P 2006/63* (2013.01); *C01P 2006/64* (2013.01); *C09C 2200/102* (2013.01); *C09C 2200/306* (2013.01); *C09C 2220/10* (2013.01)

(58) Field of Classification Search
    CPC ... C09C 1/0021; C09C 1/28; C09C 2200/102; C09C 2200/306; C09C 2220/10
    See application file for complete search history.

(56) References Cited

U.S. PATENT DOCUMENTS

| | | | |
|---|---|---|---|
| 3,874,890 A | 4/1975 | Bernhard | |
| 3,926,659 A | 12/1975 | Hesse | |
| 4,867,793 A * | 9/1989 | Franz | A61Q 1/02 106/415 |
| 6,019,831 A | 2/2000 | Emmert | |
| 2006/0144295 A1 | 7/2006 | Shiomi | |
| 2007/0032573 A1 | 2/2007 | Ino | |
| 2011/0256194 A1 | 10/2011 | Kaida | |

FOREIGN PATENT DOCUMENTS

| | | |
|---|---|---|
| JP | S4994714 | 9/1974 |
| JP | S49128027 | 12/1974 |
| JP | S587674 | 2/1983 |
| JP | S6119666 | 1/1986 |
| JP | S6216408 | 1/1987 |
| JP | S62115071 | 5/1987 |
| JP | S62174002 | 7/1987 |
| JP | S62285956 | 12/1987 |
| JP | S63265966 | 11/1988 |
| JP | H04145168 | 5/1992 |
| JP | H0832839 | 3/1996 |
| JP | H08231880 | 9/1996 |
| JP | H10316882 | 2/1998 |
| JP | 4647494 B2 | 3/2011 |
| WO | 2005028566 | 3/2005 |

OTHER PUBLICATIONS

Brief explanation of relevance of Foreign Patent Documents disclosed herewith.
Extended European Search Report dated Sep. 14, 2015 issued in the corresponding European patent application No. 13741230.0.

* cited by examiner

IRON OXIDE-COATED LAYERED SILICATE PIGMENT

RELATED APPLICATIONS

This application claims the priority of Japanese Patent Application No. 2012-11283 filed on Jan. 23, 2012, which is incorporated herein by reference.

FIELD OF THE INVENTION

The present invention relates to an iron oxide-coated layered silicate pigment, and in particular, relates to the improvement in colorability and gloss.

BACKGROUND OF THE INVENTION

Traditionally, color pigments and pearl pigments, wherein a plate particle of layered-silicate and the like is used as the base and a metal oxide such as iron oxide is coated on its surface, have been known.

For example, in patent literature 1, low-gloss black iron oxide coated black flake pigments, wherein a mica flake was used as the base of the iron-containing pigment, black iron oxide ($Fe_3O_4$) was used as the iron oxide that was coated on the surface, and the $Fe_3O_4$ was deposited on a muscovite particle itself or a muscovite particle coated with $TiO_2$ and $ZrO_2$, are described.

In addition, it is described in patent literature 2 that a nacreous pigment with a coating layer of $Fe_3O_4$ and having an interference color can be obtained by coating a platelet-shaped substrate such as mica with a smooth iron(III) oxide layer, wherein very fine crystals are uniformly and densely packed, and converting this to a layer containing iron(II) oxide by exposing to a reducing atmosphere at 100° C. or higher.

In patent literature 3, a black bright pigment wherein the surface portion of a flaky glass base is coated with a thin film, with a thickness of 10 nm to 1 μm, of $Fe_3O_4$ and/or a low-order titanium oxide is mentioned. It is described that a pigment excellent in brightness can be obtained by using flaky glass as the base because of its high surface smoothness. It is also described that if the thickness of the coating layer exceeds 300 nm, the interference color becomes weak, the development of black color becomes strong, and the concealment rate also becomes high.

However, in these conventional iron oxide-coated layered silicate pigments, gloss is low when blackness is satisfactory. On the other hand, when gloss is satisfactory, an interference color develops in addition to a black color. Accordingly, they were not entirely satisfactory in the blackness inherent in black iron oxide and in the gloss inherent in plate particles. That is, there have been no iron oxide-coated layered silicate pigments that can sufficiently satisfy both the iron oxide-inherent color and gloss.

CITATION LIST

Patent Literature

Patent literature 1: Japanese publication of examined patent application S58-7674
Patent literature 2: Japanese publication of examined patent application H08-32839
Patent literature 3: Japanese Patent No. 4647494

DISCLOSURE OF THE INVENTION

Problem to be Solved by the Invention

The present invention was made in view of the above-described background art, and the object is to provide an iron oxide-coated layered silicate pigment that has no interference color, strongly exhibits the color inherent in iron oxide, and is excellent in gloss.

Means to Solve the Problem

In the conventional iron oxide-coated layered silicate pigment, iron oxide was non-selectively coated on the entire surface portion and edge portion of a base plate particle, and iron oxide was uniformly distributed or scattered on the plate particle.

The present inventors have diligently studied; as a result, the present inventors have obtained an iron oxide-coated layered silicate pigment wherein iron oxide is preferentially/selectively coated and localized on the edge portion rather than the surface portion of a layered-silicate plate particle. The present inventors have found that this pigment is excellent in the strength of the color inherent in iron oxide and in the gloss compared with the conventional iron oxide-coated layered silicate pigment, thus leading to the completion of the present invention.

That is, the iron oxide-coated layered silicate pigment of the present invention is an iron oxide-coated layered silicate pigment comprising a layered-silicate plate particle, which acts as the base, and iron oxide that coats the above-described plate particle; the iron oxide-coated layered silicate pigment is characterized in that the above-described iron oxide does not coat the surface portion of the above-described plate particle or the iron oxide is localized on the edge portion rather than the surface portion of the above-described plate particle.

In addition, the present invention provides an iron oxide-coated layered silicate pigment characterized in that the iron oxide thickness of the edge portion, which is the thickness of iron oxide coating layer parallel to the direction of the face of the base plate particle, is larger than the iron oxide thickness of the surface portion, which is the thickness of iron oxide coating layer parallel to the direction of the thickness of the base plate particle, in the above-described pigment.

In addition, the present invention provides an iron oxide-coated layered silicate pigment characterized in that the iron oxide thickness of the edge portion is 1.5 times or more of the iron oxide thickness of the surface portion in the above-described pigment.

In addition, the present invention provides an iron oxide-coated layered silicate pigment characterized in that the entire edge portion of a base plate particle is coated with iron oxide in the pigment described in any of the above.

In addition, the present invention provides an iron oxide-coated layered silicate pigment characterized in that the surface portion of a base plate particle is not coated with iron oxide in the pigment described in any of the above.

In addition, the present invention provides an iron oxide-coated layered silicate pigment characterized in that part of the surface portion of a base plate particle is coated with iron oxide in the pigment described in any of the above.

In addition, the present invention provides an iron oxide-coated layered silicate pigment characterized in that the entire surface portion of a base plate particle is coated with iron oxide in the pigment described in any of the above.

In addition, the present invention provides an iron oxide-coated layered silicate pigment characterized in that the layered silicate is a mica-group layered silicate in the pigment described in any of the above.

In addition, the present invention provides an iron oxide-coated layered silicate pigment characterized in that the layered silicate is a synthetic mica in the above-described pigment.

In addition, the present invention provides an iron oxide-coated layered silicate pigment characterized in that iron oxide is at least one kind selected from black iron oxide ($Fe_3O_4$) and red iron oxide ($Fe_2O_3$) in the pigment described in any of the above.

In addition, the present invention provides an iron oxide-coated layered silicate pigment characterized in that iron oxide is black iron oxide ($Fe_3O_4$) in the pigment described in any of the above.

In addition, the present invention provides an iron oxide-coated layered silicate pigment characterized in that the pigment described in any of the above containing black iron oxide ($Fe_3O_4$) as the iron oxide, is oxidized and at least part of black iron oxide ($Fe_3O_4$) is converted to red iron oxide ($Fe_2O_3$).

In addition, the present invention provides an iron oxide-coated layered silicate pigment characterized in that the pigment has no interference color in the pigment described in any of the above.

In addition, the present invention provides cosmetics characterized in that an iron oxide-coated layered silicate pigment described in any of the above is contained.

Effect of the Invention

In the iron oxide-coated layered silicate pigment of the present invention, the surface portion of the layered silicate plate particle is not coated with iron oxide or iron oxide is localized on the edge portion rather than the surface portion of the above-described plate particle. As a result, the development of the color inherent in iron oxide becomes strong and the gloss is also excellent.

BEST MODE FOR CARRYING OUT THE INVENTION

The iron oxide-coated layered silicate pigment of the present invention is characterized in that a layered-silicate plate particle is used as the base and the plate particle is coated with iron oxide; however, the iron oxide does not coat the surface portion of the plate particle or the iron oxide is localized on the edge portion rather than the surface portion of the above-described plate particle.

Figure 1:
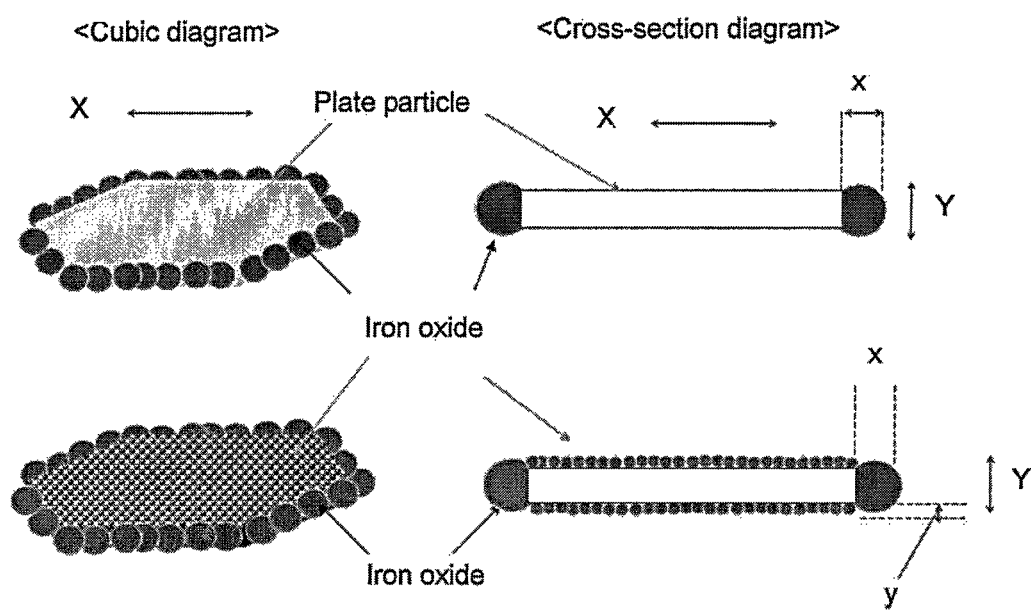
FIG. 1 is a schematic drawing of an iron oxide-coated layered silicate pigment, which is one example of the present invention.

In the present invention, "the iron oxide does not coat the surface portion of the plate particle or the iron oxide is localized on the edge portion rather than the surface portion of the above-described plate particle" means that, as shown in FIG. 1, the thickness of the iron oxide coating layer x on the plate particle edge portion, which is parallel to the direction X of the face of the base plate particle (in the present invention, this is called "iron oxide thickness of the edge portion") is larger than the thickness of the iron oxide coating layer y on the surface portion of the plate particle, which is parallel to the direction Y of the thickness of the base plate particle (in the present invention, this is called "the iron oxide thickness of the surface portion", and y may be zero). For example, in the present invention, the iron oxide thickness of the edge portion can be 1.5 times or more of the iron oxide thickness of the surface portion. In the conventional iron oxide-coated layered silicate pigment, the iron oxide thickness of the edge portion is comparable or smaller than the iron oxide thickness of the surface portion. The x and y values can be measured with an electron microscope.

In the iron oxide-coated layered silicate pigment of the present invention, it is preferable that the entire edge portion of a base plate particle is coated with iron oxide. It is considered, in this case, that the scattered light generated on the edge portion of the base plate particle is sufficiently absorbed; as a result, the gloss of the pigment improves as a whole. In order to sufficiently achieve such an effect, it is preferable that the iron oxide thickness of the edge portion is at least comparable to the thickness of the base plate particle or larger.

On the other hand, in the present invention, the iron oxide thickness of the surface portion is smaller than the iron oxide thickness of the edge portion.

On the surface portion of a base plate particle, part or the entire portion thereof may not be coated with iron oxide, and part or the entire portion of the layered silicate may be exposed. In this case, the gloss inherent in the layered silicate plate particle can be satisfactorily achieved.

Alternatively, in the iron oxide-coated layered silicate pigment of the present invention, the entire surface portion of a base plate particle may be coated with iron oxide, and the layered silicate base need not be exposed. In this case, if the iron oxide thickness of the surface portion is too thick, an interference color is generated and the color inherent in iron oxide is impaired. Therefore, in the present invention, the iron oxide thickness of the surface portion is made thin to the degree that no interference color is generated. Normally, it is preferable to allow it to be 60 nm or less. In addition, it is preferable that the coating layer of the surface portion iron oxide is of as uniform thickness as possible and the surface is relatively even. Herewith, the color inherent in iron oxide will be strongly exhibited and the gloss will also be excellent.

As the layered silicate plate particle used as the base of the present invention, a publicly known one can be used, and normally a water-non-swellable layered silicate is used.

Preferable examples include mica-group layered silicates such as muscovite and synthetic micas; synthetic micas are especially preferable because there are less impurities and the smoothness of the surface portion is also excellent. Examples include
potassium phlogopite [$KMg_3(AlSi_3O_{10})F_2$],
potassium tetrasilicic mica [$KMg_{2\ 1/2}(Si_4O_{10})F_2$],
potassium taeniolite [$KMg_2Li(Si_4O_{10}F_2$],
$K_{2/3}Mg_{2\ 1/3}Li_{2/3}(Si_4O_{10})F_2$, etc.

Synthetic micas obtained by any preparation method such as the melting method, hydrothermal method, or the inter-solid reaction method can be used. Normally, the synthetic mica powder of good crystal quality can be obtained by mixing compounds containing potassium, sodium, magnesium, aluminum, silicon, fluorine, etc. at a fixed ratio, melting the mixture, crystallizing out, mechanically crushing after cooling, heat-treating, washing, and drying.

The general production method of synthetic mica powder is as follows. Layered crystals with several mm to several cm, obtained by a melting synthesis method, are coarsely crushed with a dry crusher, such as a jaw crusher or hammer crusher and then further crushed with a fine grinding machine. For example, in the case of synthetic fluorphlogopite (potassium phlogopite), silicic anhydride, magnesium oxide, aluminum oxide, and potassium fluorosilicate are weighed and mixed, so that the above composition is attained, melted at 1,400 to 1,500° C., and cooled to room temperature to obtain synthetic fluorphlogopite. Lumps of the obtained synthetic fluorphlogopite are crushed and fractioned, if necessary, to obtain synthetic mica powder.

The particle size of the synthetic mica powder used in the present invention is not limited in particular and it can be suitably selected. Generally, the synthetic mica powder with an average particle size of 5 to 50 μm and an aspect ratio of 2 to 300 is preferably used.

In addition, it is preferable to use a layered silicate, as the base particle, that is not coated with other coating materials such as $TiO_2$.

In the iron oxide-coated layered silicate pigment of the present invention, iron oxide can be at least one kind selected from black iron oxide ($Fe_3O_4$) and red iron oxide ($Fe_2O_3$). Black iron oxide is especially preferable because scattered light at the edge portion of a base plate particle can be effectively absorbed. In addition, black iron oxide can be converted to red iron oxide by oxidation; therefore, a dark brown to reddish brown iron oxide-coated layered silicate pigment can be obtained by heat treatment of black iron oxide-coated layered silicate pigment in the atmosphere.

As the method by which black iron oxide is preferentially or selectively coated on the edge portion rather than the surface portion of a base plate particle in obtaining the iron oxide-coated layered silicate pigment of the present invention, for example,
(A) deposition method of black iron oxide ($Fe_3O_4$) by the simultaneous little-by-little addition, under stirring, of an aqueous solution containing $Fe^{2+}$ and an aqueous solution of oxidizing agent into a slurry of base plate particles can be listed.

In the above-described method (A), the pH of the slurry is kept constant between 8 and 9 during addition. For this purpose, acid or alkali is added as necessary. On this occasion, if the addition rate of the aqueous solution containing $Fe^{2+}$ is about $3.0 \times 10^{-3}$ g/min higher, in terms of $Fe_3O_4$, per 1 $m^2$ of the surface area of the base layered-silicate plate particle, the deposition on the surface portion takes place easily; therefore, it is desirable to dropwise add, as slowly as possible, at a lower addition rate than this.

In addition, it is preferable that the temperature of the slurry is kept constant between 70 to 80° C. It is also preferable that the addition is carried out while an inert gas such as nitrogen gas or argon gas is being bubbled. After the completion of addition, stirring may be continued as necessary for about 5 minutes to 2 hours while the temperature is being maintained.

Then, by dehydration, washing by water, and drying at 100° C. or lower, a black iron oxide-coated layered silicate pigment, wherein black iron oxide is preferentially/selectively coated and localized on the edge portion rather than the surface portion of a base plate particle, can be obtained. It is preferable to carry out drying under an inert gas such as nitrogen gas or argon gas.

A slurry of base plate particles can be obtained by mixing and stirring base plate particles and water. The concentration of base plate particles in the slurry is not limited in particular; however, it is normally 1 to 20 mass % and preferably 5 to 15 mass %.

An aqueous solution containing $Fe^{2+}$ can be prepared by dissolving an $Fe^{2+}$ salt such as ferrous sulfate ($FeSO_4$), ferrous chloride ($FeCl_2$), or ferrous phosphate in water. However, iron(III) oxide hydroxide deposits over time because $Fe^{2+}$ salts are unstable in water. Therefore, it is preferable to stabilize the $Fe^{2+}$ salt by strongly acidifying the pH of the $Fe^{2+}$ aqueous solution by adding an acid such as sulfuric acid, hydrochloric acid, or nitric acid.

The amount of $Fe^{2+}$ is set according to the intended amount of coating; however, it is preferable to use the amount with which at least the entire edge portion of a base plate particle can be coated. Normally, the amount of $Fe^{2+}$ is 20 mass % or higher with respect to the base plate particle in terms of $Fe_3O_4$, and preferably 30 mass % or higher (all are in inner percentages).

An aqueous solution of an oxidizing agent can be prepared by dissolving an oxidizing agent such as potassium nitrate ($KNO_3$) in water. It is preferable that the amount of the oxidizing agent is 0.3 to 1.0 times (mole ratio) with respect to the amount of $Fe^{2+}$.

According to the above-described method, a black iron oxide-coated layered silicate pigment, wherein black iron oxide is preferentially/selectively deposited and a thick coating layer is formed on the edge portion of a base plate particle and black iron oxide is not at all or hardly deposited or coated on the surface portion of a base plate particle, can be obtained.

As the method to obtain the iron oxide-coated layered silicate pigment of the present invention, wherein a black iron oxide is coated on the entire surface portion in addition to the edge portion of a base plate particle, for example, the method in which black iron oxide is preferentially/selectively coated on the edge portion, as described above, and then black iron oxide is further coated non-preferentially/non-selectively on the surface portion and edge portion or the method in which black iron oxide is non-preferentially/non-selectively coated in advance on the surface portion and edge portion of a base plate particle and then, as described above, black iron oxide is preferentially/selectively coated on the edge portion can be listed.

As the method for non-preferential/non-selective coating of black iron oxide on the surface portion and edge portion, the conventionally known coating method of black iron oxide can be used. For example,
(B) deposition method of black iron oxide ($Fe_3O_4$) by the simultaneous addition, under stirring, of an aqueous solution containing $Fe^{2+}$ and an aqueous solution containing $Fe^{3+}$ or the addition of an aqueous solution containing $Fe^{2+}$ and $Fe^{3+}$ into a slurry of base plate particles can be listed; however, it is not limited to this method.

In the above-described method (B), the pH of the slurry is kept constant between 8 and 10 during addition. For this purpose, acid or alkali is added as necessary. In addition, it is preferable that the temperature of the slurry is kept constant between 70 to 80° C. It is also preferable that the addition is carried out while bubbling an inert gas such as nitrogen gas or argon gas. The addition time is normally about 5 minutes to 1 hour. After the completion of addition, stirring may be continued as necessary for about 5 minutes to 2 hours while the temperature is being maintained.

Then, dehydration, washing by water, and drying at 100° C. or lower are carried out; thus black iron oxide can be non-preferentially/non-selectively and uniformly coated on the surface portion and edge portion of the base plate particle. It is preferable to carry out drying under an inert gas such as nitrogen gas.

A slurry of base plate particles can be obtained in the same way as above. As the base plate particle, an iron oxide-coated layered silicate pigment wherein black iron oxide is preferentially/selectively coated on the edge portion can also be used.

An aqueous solution containing $Fe^{2+}$ can be obtained in the same way as above.

An aqueous solution containing $Fe^{3+}$ can be prepared by dissolving an $Fe^{3+}$ salt, such as ferric sulfate ($Fe_2(SO_4)_3$) or ferric chloride ($FeCl_3$), in water.

It is preferable to make the $Fe^{2+}$ aqueous solution and/or $Fe^{3+}$ aqueous solution acidic, in a similar manner as described above, by adding an acid such as sulfuric acid.

The amount of $Fe^{2+}$ and the amount of $Fe^{3+}$ can be set according to the intended amount of coating; however, it is preferable to use the amounts that can coat the entire surface portion. Normally, the sum of $Fe^{2+}$ and $Fe^{3+}$ is 1 to 15 mass % (inner percentage) in terms of $Fe_3O_4$ with respect to the base plate particle.

In order to deposit black iron oxide, it is preferable to let the ratio of $Fe^{2+}$ to $Fe^{3+}$ be 0.5:1 to 1:1 (mole ratio).

Instead of separate aqueous solutions of $Fe^{2+}$ and $Fe^{3+}$, an aqueous solution containing both $Fe^{2+}$ and $Fe^{3+}$ can also be used.

In addition, at least part of black iron oxide in the black iron oxide-coated layered silicate pigment can be converted to red iron oxide ($Fe_2O_3$) by oxidation; thus a dark brown to reddish brown iron oxide-coated layered silicate pigment can be obtained.

As the oxidation method, a publicly known method can be adopted, for example, a heat treatment method, at 500 to 800° C., in an oxidizing atmosphere such as in air is easy to use.

The iron oxide-coated layered silicate pigment of the present invention can be used in the application in which the conventional iron oxide-coated layered silicate pigment has been used. For example, it is possible to blend it in cosmetics, paint, ink, resin, etc. In particular, a cosmetic with the color having both unprecedented gloss and the strong color inherent in iron oxide can be prepared by blending the pigment of the present invention into a publicly known cosmetic base. The cosmetics are not limited in particular, and examples include makeup cosmetics such as eyeshadow, eyeliner, eyebrow, lipstick, lip gloss, lip gloss, mascara, and nail enamel; and hair cosmetics such as hair dye and hair color.

The blending amount of the iron oxide-coated layered silicate pigment of the present invention is not limited in particular, and it is suitably determined according to the kinds and forms of cosmetics and the intended degree of coloring. The iron oxide-coated layered silicate pigment of the present invention is normally blended 0.05 mass % or higher in cosmetics. If the blending amount is 0.5 mass % or higher and furthermore 1.0 mass % or higher, the effect of the iron oxide-coated layered silicate pigment of the present invention is more prominently exhibited. The upper limit of the blending amount is also not limited in particular and suitably determined, and blending 100 mass % thereof into a cosmetic is possible. However, from the view point of blending of other cosmetic components and cosmetic production, it is normally 90 mass % or lower, and typically 60 mass % or lower.

EXAMPLES

Hereinafter, the present invention will be further explained with reference to specific examples; however, the present invention is not limited by these examples.

Production Example 1

The production was carried out by the below-described method.
(1) Preparation of a mica slurry:

In a beaker, 50 g of mica powder (manufactured by Topy Industries, Ltd., PDM-20L: synthetic potassium phlogopite, particle size: about 20 μm, surface area: about 2.4 m$^2$/g, aspect ratio: about 70) and 450 g of water were mixed with stirring; thus a slurry was prepared, heated, and maintained at 80° C.
(2) Preparation of an $Fe^{2+}$ aqueous solution:

Separately, an aqueous solution containing $Fe^{2+}$ was prepared so that the concentration is about 50% (inner percentage) with respect to mica in terms of $Fe_3O_4$. Specifically, 180.0 g of ferrous sulfate ($FeSO_4 \cdot 7H_2O$), 6.5 g of sulfuric acid ($H_2SO_4$), and 400 g of pure water were placed in a beaker and mixed; thus an $Fe^{2+}$ aqueous solution was prepared.
(3) Preparation of an aqueous solution of an oxidizing agent:

Into another beaker, 44.5 g of potassium nitrate ($KNO_3$), which is an oxidizing agent, and 300 g of pure water were placed and mixed; thus an aqueous solution of an oxidizing agent was prepared.
(4) Coating of the edge portion:

To (1) a slurry under stirring, (2) an $Fe^{2+}$ aqueous solution at 1.2 g/min and (3) an aqueous solution of an oxidizing agent at 0.71 g/min were simultaneously dropwise added while nitrogen gas was being bubbled. On this occasion, so that the pH of the slurry is maintained at 8.0, a NaOH aqueous solution was simultaneously dropwise added. The drop time was about 8 hours. The temperature was maintained at 80° C.

After the completion of dropwise addition, stirring was continued for 30 minutes at 80° C., and then heating and stirring were stopped.
(5) Dehydration and drying:

After the above-described process, sufficient washing with pure water was carried out, and then dehydration was carried out by suction filtration.

The obtained water-containing cake was dried by heating at 80° C. for 15 hours under a flow of nitrogen gas, and strongly-black iron oxide-coated layered silicate pigment powder with excellent gloss was obtained. An electron micrograph is shown in FIG. 2.

Figure 2:
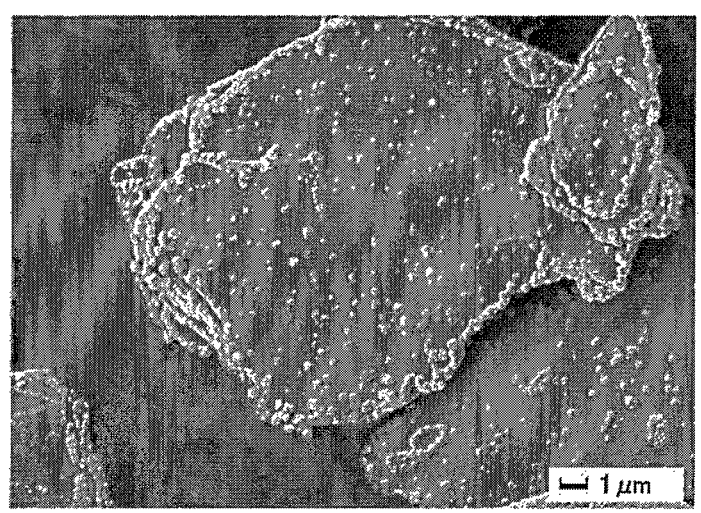
FIG. 2 is an electron micrograph of an iron oxide-coated layered silicate pigment (Production Example 1), which is one example of the present invention.

As seen from FIG. 2, in this iron oxide-coated layered silicate pigment, the entire edge portion of a base plate particle was coated with $Fe_3O_4$; however, only an extremely small amount of $Fe_3O_4$ was scattered on the surface portion of a base plate particle and the layered silicate was exposed on most of the surface portion.

As a result of iron content analysis by powder X-ray measurement and ICP, the iron oxide-coated layered silicate pigment of Production Example 1 was found to contain 49.8 mass % of $Fe_3O_4$.

Production Example 2

Figure 3:
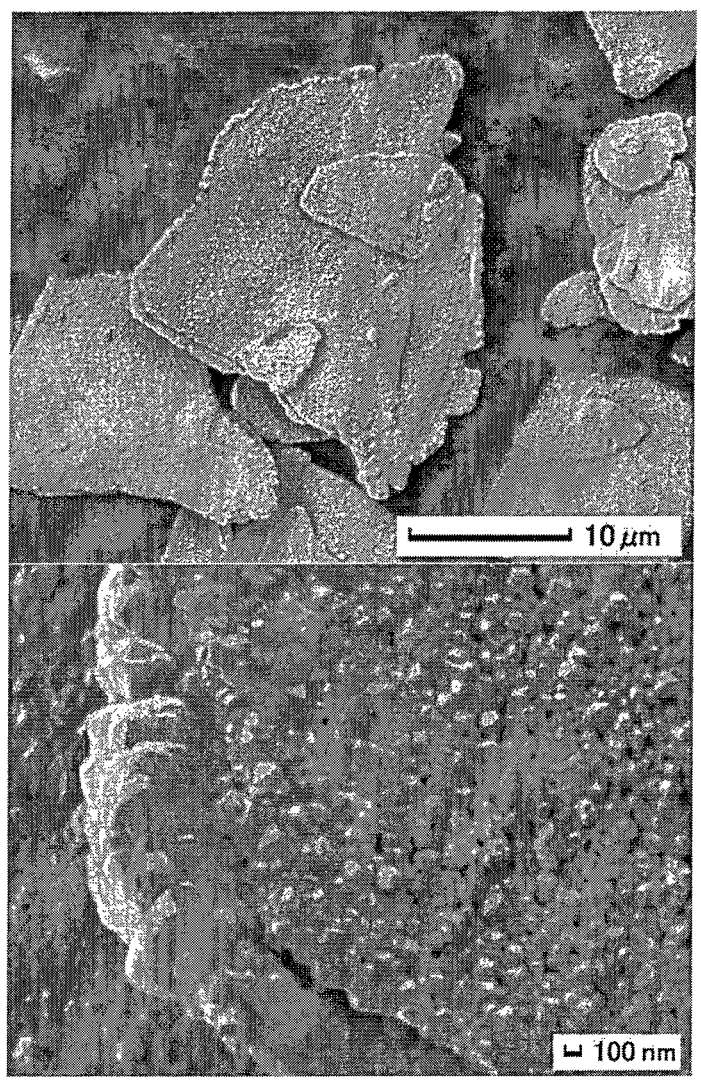
FIG. 3 is an electron micrograph of an iron oxide-coated layered silicate pigment (Production Example 2), which is one example of the present invention.

The production was carried out by the below-described method.
(1) Preparation of a mica slurry:
  In a beaker, 50 g of mica powder (manufactured by Topy Industries, Ltd., PDM-20L: synthetic potassium phlogopite, particle size: about 20 µm, surface area: about 2.4 $m^2/g$, aspect ratio: about 70) and 450 g of water were mixed with stirring; thus a slurry was prepared, heated, and maintained at 80° C.
(2) Preparation of an $Fe^{2+}/Fe^{3+}$ mixed aqueous solution:
  Separately, an aqueous solution containing $Fe^{2+}$ and $Fe^{3+}$ was prepared so that the concentration is about 11% (inner percentage) with respect to mica in terms of $Fe_3O_4$. Specifically, 7.5 g of ferrous sulfate ($FeSO_4 \cdot 7H_2O$), 26.3 g of ferric sulfate aqueous solution (41 mass % of $Fe_2(SO_4)_3$ is contained), 0.3 g of sulfuric acid ($H_2SO_4$), and 60 g of water were placed in another beaker and mixed; thus an $Fe^{2+}/Fe^{3+}$ mixed aqueous solution was prepared. (Instead of an $Fe^{2+}/Fe^{3+}$ mixed aqueous solution, an $Fe^{2+}$ aqueous solution and an $Fe^{3+}$ aqueous solution may be separately prepared by mixing ferrous sulfate and ferric sulfate into a half amount of sulfuric acid and a half amount of water, respectively, and both aqueous solutions may be simultaneously dropwise added in the following (3).)
(3) Coating of the surface portion and edge portion (non-selective coating):
  To (1) a slurry under stirring, (2) an $Fe^{2+}/Fe^{3+}$ mixed aqueous solution was dropwise added at 1.57 g/min while nitrogen gas was being bubbled. Simultaneously, a NaOH aqueous solution was also dropwise added so that the pH of the slurry is maintained at 8.0. The drop time was about 1 hour. The temperature was maintained at 80° C.
  After the completion of dropwise addition, stirring was continued for 10 minutes at 80° C., and Fe compounds were uniformly deposited on the entire surface portion and edge portion of a mica plate particle.
(4) Preparation of $Fe^{2+}$ aqueous solution:
  Separately, an aqueous solution containing $Fe^{2+}$ was prepared so that the concentration is about 50% (inner percentage) with respect to mica in terms of $Fe_3O_4$. Specifically, 180.0 g of ferrous sulfate ($FeSO_4.7H_2O$), 6.5 g of sulfuric acid ($H_2SO_4$), and 400 g of pure water were placed in a beaker and mixed; thus an $Fe^{2+}$ aqueous solution was prepared.
(5) Preparation of an aqueous solution of an oxidizing agent:
  Into another beaker, 44.5 g of potassium nitrate ($KNO_3$), which is an oxidizing agent, and 300 g of pure water were placed and mixed; thus an aqueous solution of an oxidizing agent was prepared.
(6) Coating of the edge portion:
  To the slurry obtained in (3), under stirring while nitrogen gas was being bubbled, (4) an $Fe^{2+}$ aqueous solution and (5) an aqueous solution of an oxidizing agent were, in a similar manner to Production Example 1, simultaneously dropwise added in the course of about 8 hours. On this occasion, so that the pH of the slurry is maintained at 8.0, a NaOH aqueous solution was simultaneously dropwise added. The temperature was maintained at 80° C.
  After the completion of dropwise addition, stirring was continued for 30 minutes at 80° C., and then heating and stirring were stopped.
(7) Dehydration and drying
  After the above-described process, sufficient washing with pure water was carried out, and then dehydration was carried out by suction filtration.
  The obtained water-containing cake was dried by heating at 80° C. for 15 hours under a flow of nitrogen gas, and strongly-black iron oxide-coated layered silicate pigment powder with excellent gloss was obtained. An electron micrograph is shown in FIG. 3.
  As seen from FIG. 3, in this iron oxide-coated layered silicate pigment, the entire surface portion and edge portion of the base plate particle were coated with $Fe_3O_4$, and the iron oxide thickness of the edge portion was larger than the iron oxide thickness of the surface portion (about 2 times).
  As a result of iron content analysis by powder X-ray measurement and ICP, the iron oxide-coated layered silicate pigment of Production Example 2 was found to contain 52 mass % of $Fe_3O_4$.

Comparative Example 1

Figure 4:
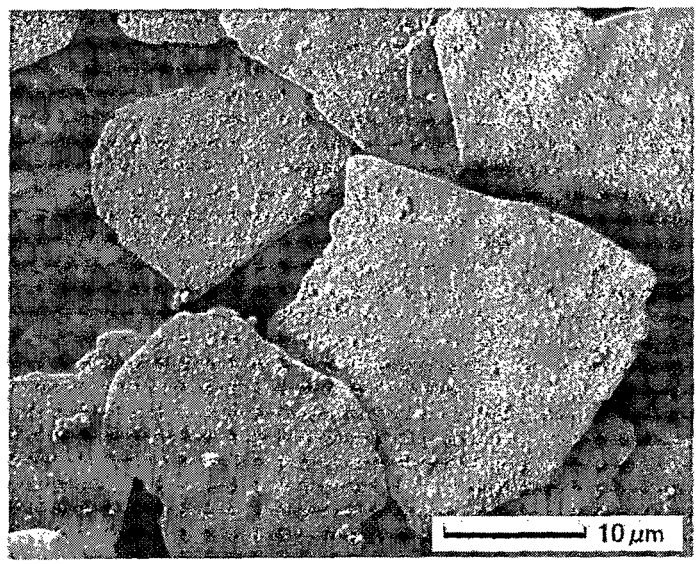
FIG. 4 is an electron micrograph of a commercial iron oxide-coated layered silicate pigment (Comparative Example 1).

Colorona® Blackstar Blue manufactured by Merck (mica uniformly coated with $Fe_3O_4$, component percentages (mass ratio): $Fe_3O_4$:mica=58:42, black-blue bright powder), particle size (80%): 10.0 to 60.0 µm, D-50:18.0 to 25.0 µm; an electron micrograph is shown in FIG. 4.

Comparative Example 2

Figure 5:
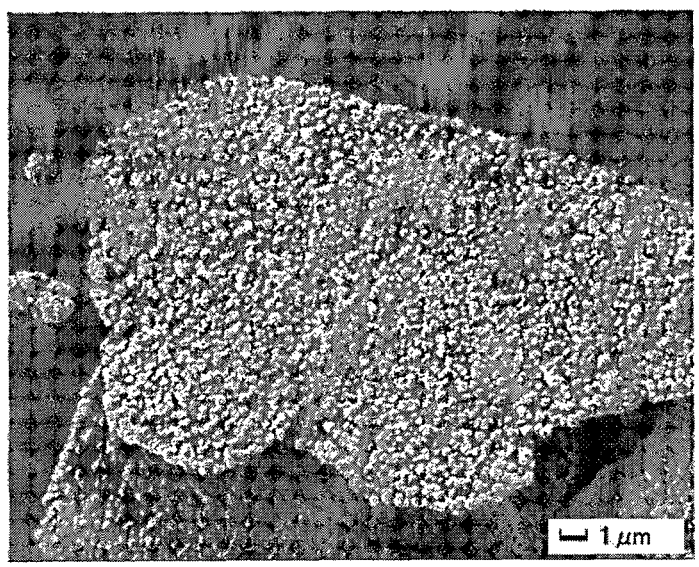
FIG. 5 is an electron micrograph of a commercial iron oxide-coated layered silicate pigment (Comparative Example 2).

Colorona® Micablack manufactured by Merck (mica coated with $Fe_3O_4$ and $TiO_2$, component percentages (mass ratio): $Fe_3O_4$:$TiO_2$:mica=50:7:43, black powder), particle size (80%): 10.0 to 60.0 µm, D-50:18.0 to 25.0 µm; an electron micrograph is shown in FIG. 5.

Comparative Example 3

Synthetic mica powder (manufactured by Topy Industries, Ltd., PDM-20L: synthetic potassium phlogopite, particle size: about 20 µm, aspect ratio: about 70) used in Production Example 1 or 2 was uniformly coated with $Fe_3O_4$ in a similar manner to Comparative Example 1.

Figure 6:
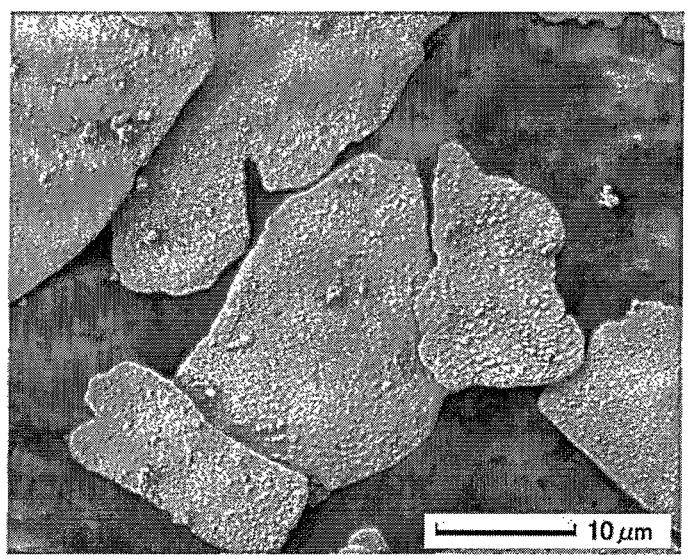
FIG. 6 is an electron micrograph of an iron oxide-coated layered silicate pigment of a comparative example (Comparative Example 3).

Specifically, a ferric chloride ($FeCl_3$) aqueous solution was dropwise added, so that the concentration is 50 mass % in terms of the inner percentage of $Fe_3O_4$, while a 10 mass % water slurry of mica was being mixed with stirring at 80° C. On this occasion, the slurry was maintained at pH=3.0 by the dropwise addition of a NaOH aqueous solution, and yellow iron oxide (FeOOH) was uniformly coated over the entire surface of mica. Then, dehydration, drying at 105° C., and the 30-minute calcination at 530° C., in the reducing atmosphere under a flow of a mixed gas of 10% $H_2$ and 90% $N_2$, were carried out; thus FeOOH coated on the mica particle surface was converted to $Fe_3O_4$ and a black-red bright pigment was obtained. An electron micrograph is shown in FIG. 6.

Comparative Example 4

Synthetic mica powder (manufactured by Topy Industries, Ltd., PDM-20L: synthetic potassium phlogopite, particle size: about 20 µm, aspect ratio: about 70) used in Production Example 1 or 2 was coated with $Fe_3O_4$ and $TiO_2$ in a similar manner to Comparative Example 2. Component percentages (mass ratio) were adjusted so that $Fe_3O_4$:$TiO_2$:mica=50:7:43.

Specifically, a water slurry of mica was heated to 70° C., and a titanium tetrachloride aqueous solution and a NaOH aqueous solution, which was suitably used to maintain the slurry at pH=1.5, were dropwise added. Thus, anatase-type $TiO_2$ was densely coated on the entire mica particle, and then dehydration, drying, and 30-minute calcination at 700° C. were carried out to obtain $TiO_2$-coated mica.

Figure 7:
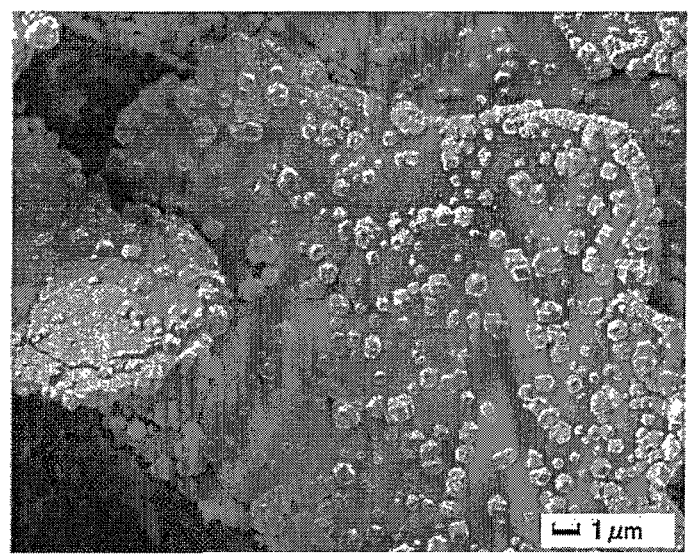
FIG. 7 is an electron micrograph of an iron oxide-coated layered silicate pigment of a comparative example (Comparative Example 4).

Subsequently, a 10 mass % water slurry of this $TiO_2$-coated mica was stirred at 80° C. under a flow of nitrogen gas, and a ferrous sulfate ($FeSO_4 \cdot 7H_2O$) aqueous solution and a potassium nitrate aqueous solution were added dropwise. On this occasion, NaOH, which was suitably used to maintain the slurry at pH=8.0, was simultaneously dropwise added in the course of about 1 hour as done in Reference Example 1 of patent literature 2. At last, dehydration and drying at 80° C. under the flow of $N_2$ gas were carried out, and a black iron oxide-coated layered silicate pigment, wherein $Fe_3O_4$ particles are scattered on the entire surface portion and edge portion of $TiO_2$-coated mica, was obtained. An electron micrograph is shown in FIG. 7.

Blackness, the presence or absence of an interference color, and the gloss of the iron oxide-coated layered silicate pigments in Production Examples 1 and 2 and Comparative Examples 1 to 4 were evaluated by the following methods. The results are shown in Table 3.

<Blackness>

A test sample was added to colorless and transparent acrylic resin paint (N Acrylic Auto Clear Super, manufactured by Nippon Paint Co., Ltd., solid content: about 50 mass %) so that the concentration in the paint was 10 mass %. After being well mixed with stirring, it was applied on a concealment rate measuring paper with an applicator with a gap of 100 μm and it was dried. The L, a, and b values of the coated film were measured with a Minolta Chroma Meter CR300. When the L value is low and a and b values are closer to zero, it indicates blackness. The color of the coated film was also observed visually.

<Gloss>

A test specimen was prepared by placing a paper double-sided tape (NICETACK®, manufactured by Nichiban Co., Ltd.) on a white thick paper, peeling off release paper, sprinkling test sample powder, smoothing with a brush until uniform to one direction, allowing the powder to be deposited on the paper double-sided tape, and lastly brushing off excess powder. Incident light was 45° with respect to the test specimen, and the L value of the light reflected at 15° to the direction of the normal, with respect to the test specimen, from 45° specular reflection (brightness: L15 value) was measured with a multi-angle spectrophotometer (MA-68II, manufactured by X-Rite, Incorporated). The higher the L15 value, the higher the brightness and it is indicative of a strong gloss.

For the above-described test specimen, gloss evaluation (sensory evaluation) by visual observation was also carried out. Specifically, 10 panelists were asked to score visual gloss impression by the criteria in Table 1 below, and the gloss was evaluated, according to the criteria in below Table 2, from the average score of 10 panelists.

TABLE 1

| Score | Impression of Gloss |
|---|---|
| 5 | There is a very strong gloss. |
| 4 | There is a strong gloss. |
| 3 | There is a slight gloss. |
| 2 | There is not much gloss. |
| 1 | There is no gloss. |

TABLE 2

| Evaluation | Average Score |
|---|---|
| A | 4 or higher |
| B | 3 or higher and less than 4 |
| C | 2 or higher and less than 3 |
| D | less than 2 |

<Interference Color>

For the test specimens prepared for the above-described gloss measurement, the presence or absence of interference color was examined by visual observation.

TABLE 3

| Test Sample | Blackness L | a | b | Visual Observation | Gloss L15 Value | Visual Observation | Interference Color |
|---|---|---|---|---|---|---|---|
| Production Example 1 | 27.07 | 0.83 | −0.5 | black | 55.1 | B | absent |
| Production Example 2 | 29.35 | 0.98 | −1.16 | black | 67.0 | A | absent |
| Comparative Example 1 | 30.18 | −0.58 | −6.29 | black-blue | 82.1 | A | present |
| Comparative Example 2 | 26.11 | 0.93 | −1.37 | black | 31.8 | D | absent |
| Comparative Example 3 | 32.48 | 10.29 | 3.38 | black-red | 81.8 | A | present |
| Comparative Example 4 | 25.11 | 0.66 | −1.31 | black | 34.2 | D | absent |

The commercial iron oxide-coated layered silicate pigment of Comparative Example 1 is a black-blue bright pigment, wherein the entire surface portion and edge portion of a mica plate particle is almost uniformly coated with an $Fe_3O_4$ layer of about 100 nm as shown in FIG. 4, and the gloss is excellent; however, it has a blue interference color and is poor in blackness.

Similarly, the synthetic mica powder coated with $Fe_3O_4$ of Comparative Example 3 is also a black-red bright pigment, wherein the entire surface portion and edge portion of a mica plate particle is almost uniformly coated with an $Fe_3O_4$ layer of about 95 nm as shown in FIG. 6, and the gloss is excellent; however, it has a red interference color and is poor in blackness.

The commercial iron oxide-coated layered silicate pigment of Comparative Example 2 is a black pigment, wherein $Fe_3O_4$ particles of about 100 to 300 nm are non-selectively scattered on the surface portion and edge portion of a mica plate particle whose surface portion and edge portion are uniformly coated with $TiO_2$ as shown in FIG. 5, and the blackness is satisfactory; however, the gloss is poor.

Similarly, the synthetic mica powder coated with $Fe_3O_4$ and $TiO_2$ of Comparative Example 4 is also a black pigment, wherein $Fe_3O_4$ particles of about 100 to 300 nm are non-selectively scattered on the surface portion and edge portion of a synthetic mica plate particle whose surface portion and edge portion are uniformly coated with TiO$_2$ as shown in FIG. 7, and the blackness is satisfactory; however, the gloss is poor.

On the other hand, the iron oxide-coated layered silicate pigment of Production Examples 1 and 2 did not show any interference color and was excellent in blackness and gloss.

The reason is not clear; however, one possibility is considered to be as follows.

Figure 8:
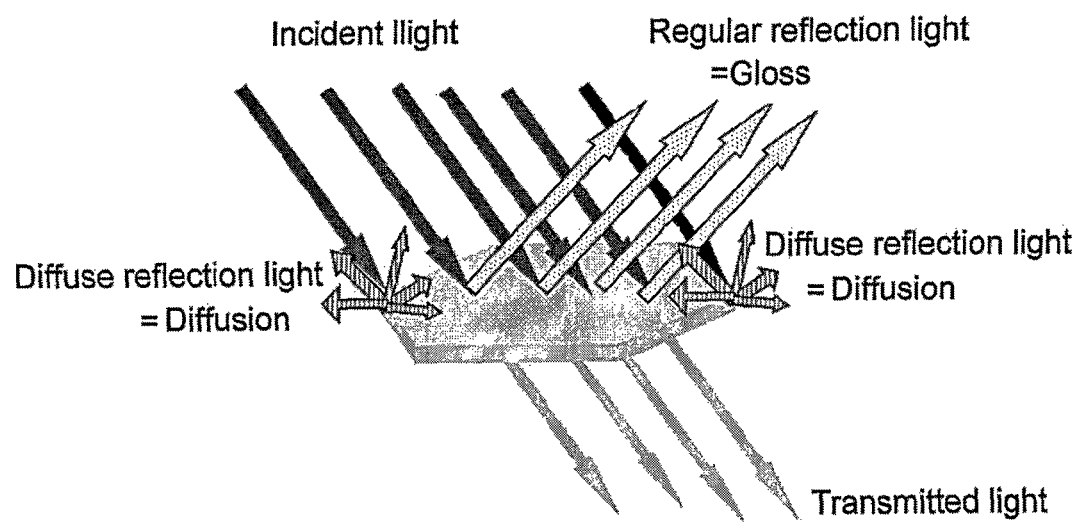
FIG. 8 is a schematic drawing that explains the development of gloss on the plate particle.

Generally, the orientation of plate particles is highly parallel. As shown in FIG. 8, the incident light to the surface portion of a plate particle is specularly reflected in a regular way to a fixed direction, and this contributes to gloss.

However, scattered light is generated by diffuse reflection of light on the edge portion of a plate particle, and this scattered light becomes a factor to decrease gloss.

In the iron oxide-coated layered silicate pigment of the present invention, such as the above-described Production Examples 1 and 2, the edge portion of a mica plate particle is coated with a thick iron oxide layer. Therefore, incident light to the edge portion is sufficiently absorbed and scattered light is hardly present; as a result, the gloss is considered to be improved.

As the reason that Production Example 2 shows a higher gloss than Production Example 1, in addition to the fact that the edge portion of a mica plate particle is coated with a thick iron oxide layer, the entire surface portion of a plate particle is coated with a uniform iron oxide layer to the extent that the interference color is not generated (about 60 nm or less); thus it is considered that the transmitted light at the surface portion in Production Example 1 is converted to a regularly reflected light, namely gloss, which is generated at the interface between mica and Fe$_3$O$_4$ on the surface portion.

As described above, the iron oxide-coated layered silicate pigment of the present invention is an iron oxide-coated layered silicate pigment wherein iron oxide layer is thickly localized on the edge portion rather than the surface portion of a plate particle, and it is excellent in gloss and displays the color inherent in iron oxide.

In the conventional iron oxide-coated layered silicate pigment, the entire surface portion and edge portion of a base plate particle are almost uniformly coated with iron oxide layer or the iron oxide particles are non-selectively scattered (partially coated) over the entire surface portion and edge portion of a plate particle. Thus far, an iron oxide-coated layered silicate pigment such as that of the present invention has not been reported.

Hereinafter, the examples of cosmetic formulations wherein the iron oxide-coated layered silicate pigment of the present invention is blended are shown. However, the present invention is not limited by these examples. The blending amount is in mass %.

All the cosmetics, wherein the iron oxide-coated layered silicate pigment obtained in Production Example 1 or Production Example 2 was blended, were excellent in the development of black color and gloss. When any pigment of Comparative Examples 1 to 4 was used instead of the iron oxide-coated layered silicate pigment, the development of black color or gloss was poorer compared with the cosmetic of the present invention.

Formulation Example 1

Cream Mascara (O/W)

| <Part A> | |
|---|---|
| Water | 51.90 mass % |
| Hydroxyethyl cellulose | 0.70 |
| Triethanolamine | 2.00 |
| <Part B> | |
| Baycusan$^{(R)}$ C1000 | 11.60 |
| (Manufactured by Bayer MaterialScience Ltd., aqueous polyurethane dispersion) | |
| <Part C> | |
| Glyceryl stearate | 2.50 |
| Carnauba wax | 10.00 |
| Stearic acid | 5.00 |
| Phenoxyethanol | 0.50 |
| Methylparaben | 0.20 |
| Propylparaben | 0.10 |
| <Part D> | |
| Iron oxide-coated layered silicate pigment | 15.00 |
| <Part E> | |
| Methylpolysiloxane | 0.50 |
| (Manufactured by Shin-Etsu Chemical Co., Ltd., KF-96A-350cs) | |

<Preparation>

Hydroxyethyl cellulose was completely hydrated and dispersed so that Part A is uniform; subsequently, Part A was heated to 80° C. To this Part A, Part B was added with stirring (phase I).

In another container, Part C was heated to 80° C. and dissolved completely. Then, Part E was added while stirring Part C (phase II).

Phase II was slowly added to phase I and emulsified at 80° C. for 15 minutes. Then, the emulsion was cooled, and Part D was added halfway at 45° C. to the emulsion and mixed. The emulsion was further cooled to 25° C., and O/W type cream mascara was obtained.

Formulation Example 2

Eyeshadow

| <Part A> | |
|---|---|
| Iron oxide-coated layered silicate pigment | 34.00 mass % |
| Talc | 50.00 |
| Magnesium stearate | 2.02 |
| Ethylparaben | 0.08 |
| <Part B> | |
| BELSIL$^{(R)}$ CDM3526VP | 1.50 |
| (manufactured by Wacker Asahikasei Silicone Co., Ltd., alkyl (C26-28) dimethicone) | |
| BELSIL$^{(R)}$ RG90 | 5.00 |
| (manufactured by Wacker Asahikasei Silicone Co., Ltd., a mixture of isododecane and (vinyldimethyl/trimethylsiloxysilicate stearyl dimethicone) copolymer) | |
| BELSIL$^{(R)}$ PDM350VP | 3.00 |
| (manufactured by Wacker Asahikasei Silicone Co., Ltd., trimethylsiloxyphenyl dimethicone) | |
| Isododecane | 4.00 |

<Preparation>

The entire components of Part A were uniformly mixed with a mixer.

In another container, BELSIL® RG90 was dissolved into isododecane of Part B, BELSIL® PDM350VP and BELSIL® CDM3526VP were added, and Part B was completely dissolved by heating to 40° C.

Subsequently, Part A was poured into Part B and uniformly mixed with a Disper. Then, the mixture was poured into a mold container and pressurized at 30 bar for 1 minute 30 seconds; thus eyeshadow was obtained.

Formulation Example 3

Nail Enamel

| <Part A> | |
|---|---|
| Nitrocellulose | 18.00 mass % |
| Toluenesulfonamide resin | 6.00 |
| Acetyl tributyl citrate | 6.00 |
| Alkyl acrylate copolymer | 2.00 |
| <Part B> | |
| Isopropanol | 5.00 |
| Benzyldimethylammonium hectorite | 2.00 |
| Ethyl acetate | 20.00 |
| Butyl acetate | 31.00 |
| <Part C> | |
| Iron oxide-coated layered silicate pigment | 10.00 |

<Preparation>

Part A was kneaded with a roller mill and homogenized; then Part B was added and uniformly dispersed with a Disper. Subsequently, Part C was poured, uniformly dispersed again with a Disper, and then filled into a designated container; thus nail color was obtained.

What is claimed is:

1. An iron oxide-coated layered silicate pigment comprising: a layered-silicate plate particle as a base, and an iron oxide coated on the plate particle;
   wherein the iron oxide does not coat the surface portion of the plate particle or the iron oxide thickness of the edge portion, which is the thickness of iron oxide coating layer parallel to the direction of the face of the base plate particle, is 1.5 times or more of the iron oxide thickness of the surface portion, which is the thickness of iron oxide coating layer parallel to the direction of the thickness of the base plate particle; and
   wherein the silicate pigment has no interference color.

2. The iron oxide-coated layered silicate pigment of claim 1, wherein the entire edge portion of the base plate particle is coated with the iron oxide.

3. The iron oxide-coated layered silicate pigment of claim 1, wherein the surface portion of the base plate particle is not coated with the iron oxide.

4. The iron oxide-coated layered silicate pigment of claim 1, wherein only a part of the surface portion of the base plate particle is coated with the iron oxide.

5. The iron oxide-coated layered silicate pigment of claim 1, wherein the entire surface portion of the base plate particle is coated with the iron oxide.

6. The iron oxide-coated layered silicate pigment of claim 1, wherein the layered silicate is a mica-group layered silicate.

7. The iron oxide-coated layered silicate pigment of claim 6, wherein the layered silicate is a synthetic mica.

8. The iron oxide-coated layered silicate pigment of claim 1, wherein the iron oxide is at least one kind selected from black iron oxide ($Fe_3O_4$) and red iron oxide ($Fe_2O_3$).

9. The iron oxide-coated layered silicate pigment of claim 1, wherein the iron oxide is black iron oxide ($Fe_3O_4$).

10. An iron oxide-coated layered silicate pigment obtained by oxidization of the iron oxide-coated layered silicate pigment of claim 1 containing black iron oxide ($Fe_3O_4$) as the iron oxide, to be converted at least part of the black iron oxide ($Fe_3O_4$) to red iron oxide ($Fe_2O_3$).

11. A cosmetic comprising the iron oxide-coated layered silicate pigment of claim 1.

12. The iron oxide-coated layered silicate pigment of claim 2, wherein the surface portion of the base plate particle is not coated with the iron oxide.

13. The iron oxide-coated layered silicate pigment of claim 2, wherein only a part of the surface portion of the base plate particle is coated with the iron oxide.

14. The iron oxide-coated layered silicate pigment of claim 2, wherein the entire surface portion of the base plate particle is coated with the iron oxide.

* * * * *